United States Patent [19]

Geithman et al.

[11] 4,122,724

[45] Oct. 31, 1978

[54] SWEPT FREQUENCY AUDIBLE BOND TESTER

[75] Inventors: Glenn A. Geithman, Renton; Wayne E. Woodmansee, Seattle, both of Wash.

[73] Assignee: The Boeing Company, Seattle, Wash.

[21] Appl. No.: 809,871

[22] Filed: Jun. 24, 1977

[51] Int. Cl.$^2$ ............................................ G01N 29/04
[52] U.S. Cl. ................................................... 73/588
[58] Field of Search ................... 73/552, 67.2, 67.7, 73/67.5 R, 67.8 R, 584, 585, 588, 582, 643, 645, 646

[56] References Cited

U.S. PATENT DOCUMENTS

| | | | |
|---|---|---|---|
| 2,824,979 | 2/1958 | McKee | 73/67.8 R |
| 2,846,874 | 8/1958 | Horn | 73/67.8 R |
| 3,531,982 | 10/1970 | Clotfelter et al. | 73/67.2 |
| 3,564,903 | 2/1971 | Woodmansee et al. | 73/67.2 |

OTHER PUBLICATIONS

Booth, "Sweep Random Vibration", *MB Vibration Notebook*, vol. 9, No. 1, pp. 4–8, Feb., 1963.

*Primary Examiner*—Stephen A. Kreitman
*Attorney, Agent, or Firm*—Conrad O. Gardner; B. A. Donahue

[57] ABSTRACT

A system for inspection of bonded structures utilizing an electromagnetic transmitting transducer for transmitting at an audio frequency which is varied linearly from $10^2$ to $10^4$ Hz with a repetition rate which is variable from 2 Hz to 50 Hz into a part being tested and including a condenser microphone also coupled to the part for providing in a receiver circuit an audible output which enables the operator to distinguish a change in the audio spectrum representative of a disbond condition.

2 Claims, 4 Drawing Figures

SWEPT FREQUENCY AUDIBLE BOND TESTER

This invention relates to the inspection of materials by means of mechanical vibrations at audio frequencies and more particularly, adhesively bonded aircraft structures of a "compliant" nature, such as fiber glass honeycomb and structures having compliant facesheets, as contrasted to "stiffer" structure in which the resonant frequency of the disbond area is higher and outside the audio range.

Heretofore, ultrasonic work piece thickness inspection has been performed as exemplified in U.S. Pat. No. 3,050,989 by transmitting a frequency and amplitude modulated tone burst into the test article with variations in amplitude of the internal vibration of the test article being detected and displayed on an oscilloscope as representative of the thickness of the test article. Also representative of the prior art are U.S. Pat. Nos. 2,824,979; 2,522,924; 2,499,459; and 2,605,633, in which crystals are utilized as vibration elements and test vibrations are at natural resonance frequencies of the crystals.

In contrast, the present system utilizes transmitting and receiving circuits, including an electromagnetic transmitting transducer and a receiving transducer comprising a condenser microphone for generating and processing at an audio frequency varied linearly from $10^2$ to $10^4$ Hz with a repetition rate which is variable from 2 Hz to 50 Hz for providing detection of a disbond area having a resonant frequency in the audio frequency range of $10^2$ to $10^4$ Hz.

Accordingly, it is an object of this invention to provide a system for inspection of materials wherein an altered vibrational spectrum representative of a disbond condition is provided in an audio output device for analysis by the ear of the operator.

It is yet another object of the invention to provide an inspection system wherein a swept audio frequency oscillator includes means for providing an adjustable sweep rate.

Other objects and advantages will become apparent from the following description taken in conjunction with the accompanying drawings in which.

Figure 1:
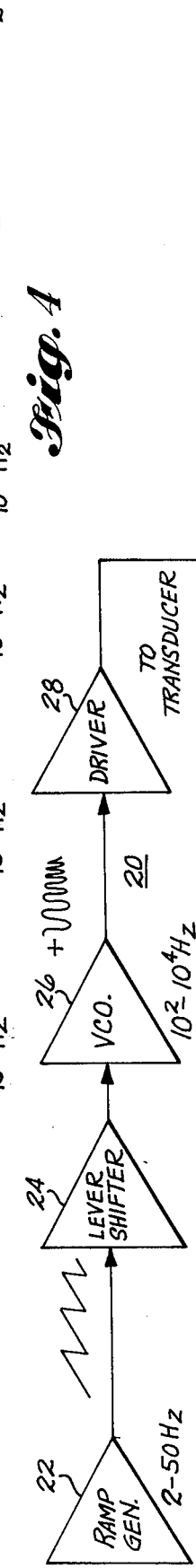
FIG. 1 is a block diagram of an embodiment of the present non-destructive inspection system.
Figure 1:
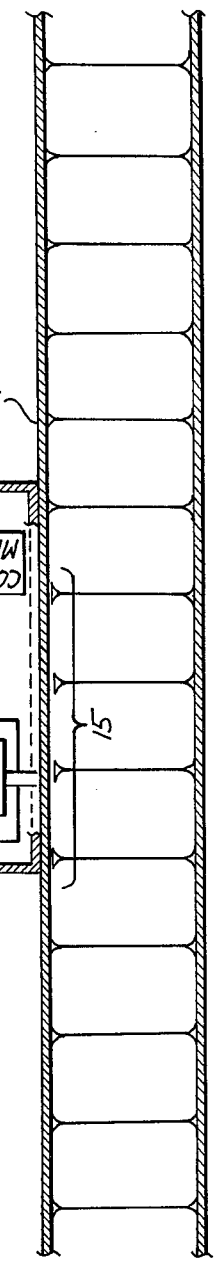

Turning now to the system of FIG. 1, it can be observed from the functional block diagram that a receiving channel 10 is coupled to receive signals from a condenser microphone 12 (which may comprise a catalog No. 33-1056 condenser microphone manufactured by Realistic enclosed in probe housing 13 disposed for inspection above disbond area 15 of fiber glass honeycomb structure 17. The output of receiving channel 10 is coupled to an audio output device comprising an 8-ohm impedance headset 14. Transmitting channel 20 of FIG. 1 (shown in detailed schematic form in FIG. 2) is seen to comprise a first stage ramp generator circuit 22 having a repetition rate which is adjustable over the range 2 to 50 Hz. The output of ramp generator circuit 22 is coupled to level shifting circuit 24 for driving voltage controlled oscillator circuit 26 linearly over the audio frequency range of $10^2$ to $10^4$ Hz, which swept frequency audio output signal from voltage controlled oscillator circuit 26 is coupled through driver amplifier circuit 28 to an electromechanical transducer of an electromagnetic type comprising electromagnetic voice coil assembly 30 (obtained from a small permanent magnetic speaker) enclosed in probe housing 13, which causes physical coupling of mechanical vibrational output from the electromechanical transducer to fiber glass honeycomb structure 17 undergoing inspection.

Figure 4:
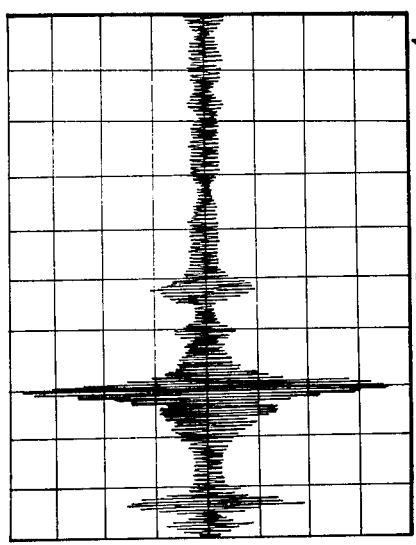
Figure 3:
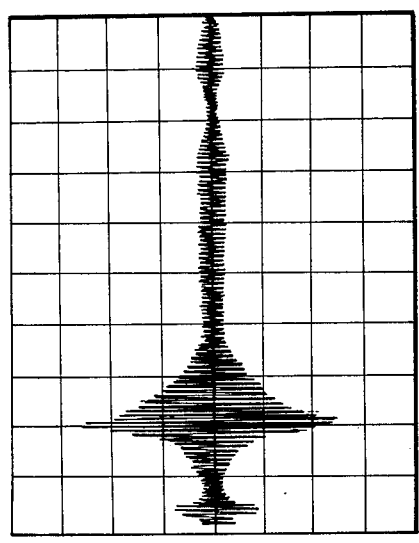
FIG. 3 is a graph representative of the swept audio spectrum output from the system of FIGS. 1 and 2 resulting from inspection of an undamaged bonded fiber glass structure; and, FIG. 4 is a graph representative of the swept audio spectrum output from the system of FIGS. 1 and 2 resulting from inspection of the same structure as FIG. 3, however, having a disbond condition.
Figure 2:
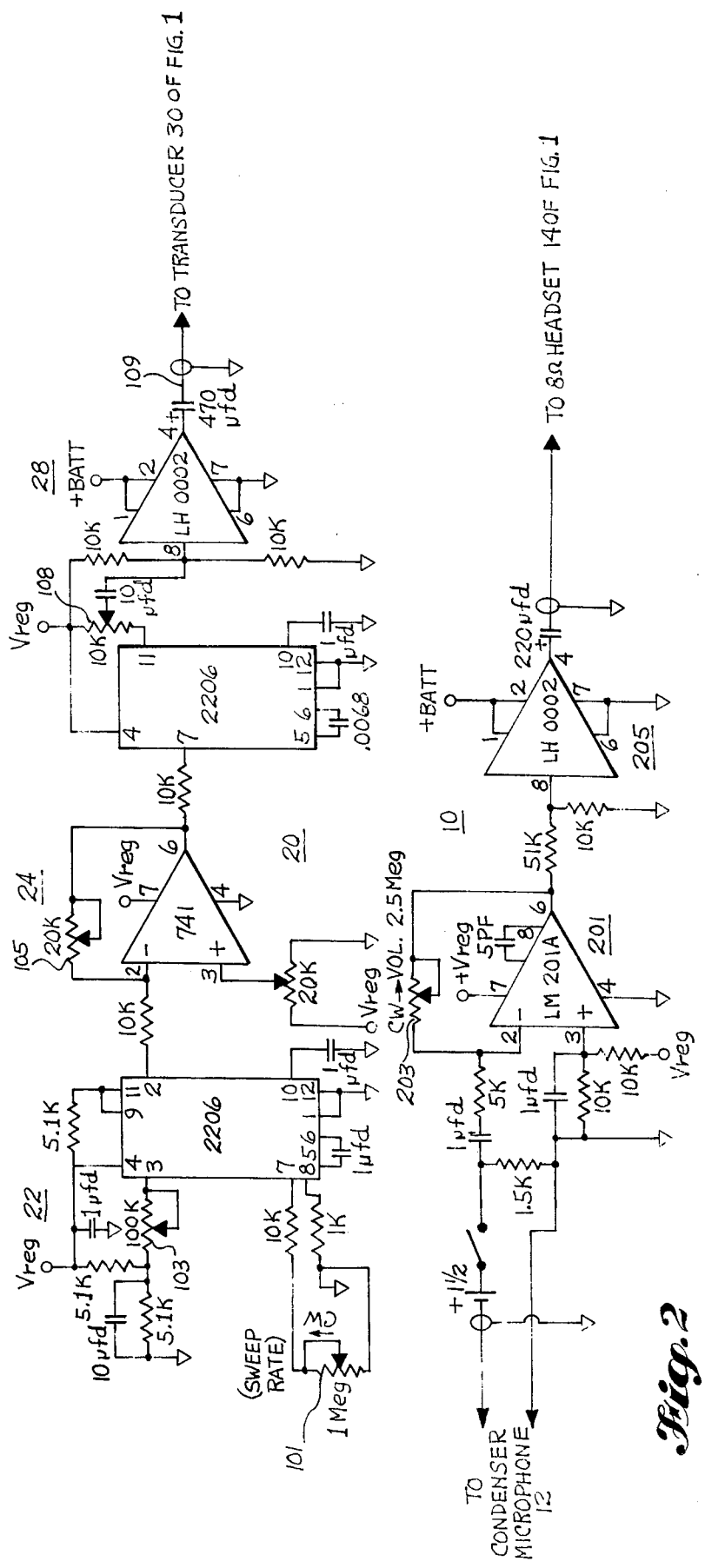
FIG. 2 is a detailed circuit schematic diagram of the system shown in FIG. 1.

Turning now to the detailed circuit schematic implementation of FIG. 1 shown in FIG. 2, it will be noted that the first stage in transmitting channel 20 comprises a pulse generating circuit comprising ramp generator circuit 22, variable from 2 to 50 Hz, which provides linear sweeping of the driving frequency of voltage controlled oscillator circuit 26. By so sweeping the driving frequency, different structures may be inspected without control adjustments in transmitting channel 20. Level shifting circuit 24, comprising an operational amplifier circuit, drives voltage controlled oscillator circuit 26 with the final stage 28 providing a low impedance output for transmitting channel 20 to drive transducer 30 (shown in FIG. 1). The sweep rate in transmitting channel 20 is controlled by adjustment of variable resistor 101, while adjustment of variable resistor 103 provides the linear sawtooth sweep signal in ramp generator circuit 22. Adjustment of variable resistor 105 controls D.C. offset in level shifting circuit 24, while adjustment of variable resistor 107 controls sawtooth amplitude, and variable resistor 108 adjustment controls the output signal at output terminal 109 of transmitting channel 20 to 1 volt peak-to-peak for coupling to transmitting transducer 30 (shown in FIG. 1). Terminals denoted $V_{reg}$ in transmitting channel 20 and receiving channel 10 are coupled to a regulated source of 3.1 volts, while + batt in receiving channel 10 is connected to a d.c. source of 12.5 volts. In receiving channel 10, voltage gain is provided by operational amplifier circuit 201 provided with variable resistor 203 for volume control in headset 14 (of FIG. 1), which operational amplifier circuit 201 drives buffer stage 205, supplying excitation voltage to headset 14 (shown in FIG. 1). Operation of the system of FIG. 2 is provided by adjustment of the aforementioned volume and sweep controls 203 and 101, respectively, while probe housing 13 (shown in FIG. 1) is positioned with slight downward pressure over the region 15 of structure 17 being inspected. FIGS. 3 and 4 show swept audio frequency spectrum provided as input to headphones 14 in the case of undamaged and disbond structures, respectively, and it can be observed therefrom by comparison thereof that the relative strengths and location of resonant peaks are indicative of the existence of a disbond condition. The human ear is acutely aware of such subtle changes of this kind occurring in the audio spectrum and thus a feature of the present system includes audio output readout, comprising headphones 14, facilitating inspection and permitting operator effort to be applied to movement of probe 13.

We claim:

1. Apparatus for sonic inspection of a work piece comprising:

a receiving transducer element comprising a condenser microphone adapted to be positioned in acoustically coupled relationship to the work piece;

receiver circuit means connected to said condenser microphone for providing an audio output signal having a vibrational spectrum responsive to detection of a flaw condition in said work piece;

a transmitting transducer element comprising an electromechanical transducer adapted to be positioned in acoustically coupled relationship to the work piece; and, transmitter circuit means connected to said electromechanical transducer for providing an input signal to said electromechanical transducer having an audio frequency which is varied linearly from about $10^2$ to $10^4$ Hz with a repetition rate which is variable from about 2 Hz to about 50 Hz.

2. Apparatus for sonic inspection of a work piece comprising:

receiving and transmitting transducer elements adapted to be positioned in acoustically coupled relationship to the work piece;

a transmitter circuit including a swept frequency oscillator circuit having an adjustable sweep rate coupled to said transmitting transducer element wherein said swept frequency oscillator circuit includes a ramp generator circuit having a sweep rate adjustable over the range from about 2Hz to about 50Hz and said swept frequency oscillator circuit is swept linearly over the audio frequency range from about $10^2$ to $10^4$ Hz;

said receiving transducer element comprising a condenser microphone;

a receiver circuit coupled to said condenser microphone for providing audio output signals wherein altered vibrational spectrum including relative strengths and location of resonant peaks is representative of movement of said transmitting transducer element from a defect-free region to a defect region in said work piece.

* * * * *